(12) United States Patent
Lee et al.

(10) Patent No.: US 9,149,505 B2
(45) Date of Patent: Oct. 6, 2015

(54) PHARMACEUTICAL COMPOSITION FOR SUPPRESSING ANGIOGENESIS, AND METHOD FOR SCREENING ACTIVE MATERIAL FOR SUPPRESSING ANGIOGENESIS

(75) Inventors: Yoon Jin Lee, Seoul (KR); Yun-Sil Lee, Seoul (KR); Hae-June Lee, Hwaseong-si (KR); Seo-Hyun Choi, Seoul (KR); Kyeng-Jung Kim, Seoul (KR)

(73) Assignee: Korea Institute of Radiological & Medical Sciences, Seoul (KR)

( * ) Notice: Subject to any disclaimer, the term of this patent is extended or adjusted under 35 U.S.C. 154(b) by 0 days.

(21) Appl. No.: 13/817,738

(22) PCT Filed: Aug. 18, 2011

(86) PCT No.: PCT/KR2011/006066
§ 371 (c)(1),
(2), (4) Date: Feb. 19, 2013

(87) PCT Pub. No.: WO2012/023811
PCT Pub. Date: Feb. 23, 2012

(65) Prior Publication Data
US 2013/0184336 A1 Jul. 18, 2013

(30) Foreign Application Priority Data
Aug. 18, 2010 (KR) .................. 10-2010-0079858

(51) Int. Cl.
*A61K 38/17* (2006.01)
*G01N 33/574* (2006.01)
(Continued)

(52) U.S. Cl.
CPC ............. *A61K 38/1709* (2013.01); *C07K 16/18* (2013.01); *G01N 33/57407* (2013.01); *G01N 33/57484* (2013.01); *A61K 48/00* (2013.01); *C07K 2317/76* (2013.01)

(58) Field of Classification Search
None
See application file for complete search history.

(56) References Cited

U.S. PATENT DOCUMENTS

| 2001/0049357 | A1 | 12/2001 | De et al. |
| 2008/0311145 | A1 | 12/2008 | Campion et al. |
| 2009/0054340 | A1* | 2/2009 | Chen et al. ....................... 514/12 |

FOREIGN PATENT DOCUMENTS

| KR | 10-2005-0050111 | 3/2005 |
| KR | 10-2006-0129025 | 8/2006 |
| WO | WO 2008/153237 | 12/2008 |

OTHER PUBLICATIONS

Piotrowicz et al., Heat shock protein 27 kDa expression and phosphorylation regulates endothelial cell migration., The FASEB Journal (1998) vol. 12, No. 14, pp. 1481-1490.*

(Continued)

*Primary Examiner* — Alexander Kim
(74) *Attorney, Agent, or Firm* — Klarquist Sparkman, LLP (57) ABSTRACT

The present invention provides a pharmaceutical composition for suppressing angiogenesis, containing heat shock protein 27 (HSP27) or a nucleic acid encoding HSP27. In addition, the present invention provides a pharmaceutical composition for treating cancer, containing HSP27 or a nucleic acid encoding HSP27. Additionally, the present invention provides a method of suppressing the in vitro growth of endothelial cells using HSP27. Further, the present invention provides a method of screening an active material for suppressing angiogenesis or an active material for treating cancer, comprising the following steps: processing endothelial cell lines into samples, respectively; measuring the content of HSP27 in an endothelial cell line; and selecting the sample in which the content of HSP27 in an endothelial cell line is increased compared with a control group.

5 Claims, 5 Drawing Sheets

(51) Int. Cl.
 *C07K 16/18* (2006.01)
 *A61K 48/00* (2006.01)

(56) References Cited

OTHER PUBLICATIONS

Nakamura et al., Serum levels of vascular endothelial growth factor are increased and correlate with malnutrition, immunosuppression involving MDSCs and systemic inflammation in patients with cancer of the digestive system., Oncology Letters (2013), vol. 5 Issue 5, pp. 1792-1074.*

Esser et al., Vascular endothelial growth factor induces VE-cadherin tyrosine phsophrylation in endothelial cells., Journal of Cell Science (1998), vol. 111, pp. 1853-1865.*

Huot et al., Oxidative stress-induced actin reorganization mediated by the p38 mitogen-activated protein kinase/heat shock protein 27 pathway in vascular endothelial cells., Circ Res. (1997), vol. 80(3), pp. 383-392.*

Carmeliet et al., "Angiogenesis in cancer and other diseases," *Nature*, 407:249, 9 pp., 2000.

Evans et al., "Vascular endothelial growth factor induces heat shock protein (HSP) 27 serine 82 phosphorylation and endothelial tubulogenesis via protein kinase D and independent of p38 kinase," *Cellular Signaling*, 20, pp. 1375-1384, 2008.

International Search Report issued Apr. 4, 2012, by the Korean Intellectual Property Office, for International Application No. PCT/KR2011-006066, filed Aug. 18, 2011, 2 pp.

NCBI Reference Sequence: NM_001540.3, "*Homo sapiens* heat shock 27kDa protein 1 (HSPB1), mRNA," downloaded from http://www.ncbi.nlm.nih.gov/nuccore/NM_001540.3 4 pp., Jan. 24, 2013.

NCBI Reference Sequence: NP_001531.1, "heat shock protein beta-1 [*Homo sapiens*]," downloaded from http://www.ncbi.nlm.nih.gov/protein/NP_001531.1, 7 pp., Jan. 24, 2013.

Lee et al., "HSP25 inhibits radiation-induced apoptosis through reduction of PKCδ-mediated ROS production," *Oncogene*, 24:3715-25, May 26, 2005.

Written Opinion of the International Searching Authority, issued Mar. 29, 2012, by the Korean Intellectual Property Office, for International Application No. PCT/KR2011-006066, filed Aug. 18, 2011, 4 pp.

* cited by examiner

PHARMACEUTICAL COMPOSITION FOR SUPPRESSING ANGIOGENESIS, AND METHOD FOR SCREENING ACTIVE MATERIAL FOR SUPPRESSING ANGIOGENESIS

CROSS REFERENCE TO RELATED APPLICATIONS

This is the U.S. National Stage of International Application No. PCT/KR2011/006066, filed Aug. 18, 2011, which in turn claims priority to and the benefit of Korean Patent Application No. 10-2010-0079858, filed Aug. 18, 2010, which is hereby incorporated by reference in its entirety.

TECHNICAL FIELD

The present invention relates to a pharmaceutical composition for inhibiting (or suppressing) angiogenesis and a method of screening active substances for inhibiting angiogenesis, and more particularly, to a pharmaceutical composition for inhibiting angiogenesis, containing a heat shock protein (HSP), which is revealed to impede growth of vascular endothelial cells, a pharmaceutical composition for treating cancer, a method of screening active substances for inhibiting angiogenesis by selecting a material increasing an amount of the HSP, and a method of screening active substances for treating cancer by selecting the material increasing an amount of the HSP.

BACKGROUND ART

Angiogenesis is a process of forming new capillaries as endothelial cells of pre-existing blood vessels decompose extracellular matrix, migrate, divide, and differentiate to form new capillaries, which does not occur except in a particular case, such as growth, reproduction, or healing wounds. However, excessive angiogenesis has been reported in diseases such as growth and metastasis of a malignant tumor, age-related macular degeneration, rheumatoid arthritis, diabetic retinopathy, psoriasis, and chronic inflammation (Cameliet and Jain, Nature, 407:249, 2000). In this regard, the treatment of angiogenesis-related ailments, particularly treating a malignant tumor, using an angiogenesis inhibitor, has been studied (WO2008153237).

Formation of blood vessel requires a complicate set of processes including growth, migration, and division of vascular endothelial cells, and formation of capillaries, and many vascular endothelial growth factors and vascular endothelial inhibition factors involved in the set of processes have been discovered. The vascular endothelial inhibition factors are activated against activity of the vascular endothelial growth factors, which are necessary in the formation of blood vessel. The vascular endothelial inhibition factors naturally existing in a body is less toxic, and thus may be used in pathological inhibition of new blood vessel formation. Therefore, many pharmaceutical products related to the pathological inhibition of new blood vessel formation are under development.

A vascular endothelial growth factor (VEGF) is a typical protein controlling formation of blood vessel. The VEGF controls new blood vessel formation from differentiation of endothelial precursor cells (angioblasts) in situ, is expressed in gestational tissue, macrophages, and hyperplastic epidermal keratinocytes during would healing, and may become a cause of tissue edema related to inflammation. According to an in situ hybridization research, it has been proved that the VEGF is highly expressed in a plurality of human tumor cell lines including glioblastoma multiforme, hemangioblastoma, central nervous system neoplasms and AIDS-related kaposi's sarcoma (WO2008153237).

The VEGF combines with a VEGF receptor 1, 2, or 3 (VEGFR1, VEGFR2, or VEGFR3) present in vascular endothelial cells, induces tyrosine phosphorylation of the VEGF receptor, and brings activation of the vascular endothelial cells, and thus consequently, the VEGF has a profound effect on the process of angiogenesis. Among them, phosphorylation of VEGFR2 serves as the most important receptor in an angiogenesis signal transduction mechanism. The VEGF is up-regulated in malignant tumor cells in which angiogenesis is involved, and the VEGF receptor is also up-regulated in tumor-infiltrating vascular endothelial cells, but expression of a VEGF and its receptor in normal cells unrelated to angiogenesis is low. Accordingly, in such normal cells, interaction between the VEGF and its receptor is blocked, and angiogenesis is inhibited, and thus tumor growth does not occur.

A high level of VEGFR2 is expressed by epidermal cells infiltrating into glioma and specifically up-regulated by VEGF produced from human glioblastoma. Since VEGFR2 transcript is almost not detected in normal cerebrovascular endothelial cells, the high level of VEGFR2 expressed in gliblastoma related epithelial cells (GAEC) indicates inducement of receptor activity during tumor formation.

Therefore, research for treating cancer by inhibiting an activity of VEGF expressed at a tumor growing area to suppress angiogenesis and thus inhibit growth of a tumor, has actively progressed. Among medications using the VEGF as a target, the most typical medication that is clinically used is Avastin™, which corresponds to a VEGF neutralizing antibody and is approved by the FDA as an anti-tumor agent.

Heat shock protein 27 which is a protein with a low molecular weight and has a charperon activity, self-aggregates to form clusters with respect to external environment factors, such as free radicals, heat, toxins, or the like, and thus has a defense ability to the external environment factors (NCBI Gene Bank Accession Number: NP_001531.1). Secretion of HSP27 with a low molecular weight (HSP27 is produced in a human, and HSP25 is produced in a rat) has been confirmed by the present inventors. Many functions of the HSP27 are known, for example, the HSP27 combines with a protein inducing apoptosis of cancer cells and increases resistance of cancer cells to radiation and anticancer drugs (Oncogene. 2005 May 26; 24(23):3715-25). However, the relationships of HSP27 with VEGF function inhibition, angiogenesis inhibition, or cancer treatment are not known.

DETAILED DESCRIPTION OF THE INVENTION

Technical Problem

The inventors have studied to invent a material effective for inhibiting angiogenesis and discovered for the first time that HSP27 inhibits growth of vascular endothelial cells by inhibiting the activation of VEGFR2 induced by VEGF. Based on this discovery, the inventors have developed a composition for inhibiting angiogenesis and a method of screening active substances for inhibiting angiogenesis.

Thus, the present invention provides a new pharmaceutical composition for inhibiting angiogenesis.

The present invention also provides a pharmaceutical composition for treating cancer.

The present invention also provides a method of inhibiting growth of vascular endothelial cells in vitro.

The present invention also provides a method of screening active substances for inhibiting angiogenesis.

The present invention also provides a method of screening active substances for treating cancer.

Technical Solution

According to an aspect of the present invention, there is provided a pharmaceutical composition for inhibiting angiogenesis, the pharmaceutical composition comprising heat shock protein 27 (HSP27).

According to another aspect of the present invention, there is provided a pharmaceutical composition for treating cancer, wherein the pharmaceutical composition comprises HSP27.

According to another aspect of the present invention, there is provided a pharmaceutical composition for inhibiting angiogenesis, comprising a nucleic acid coding HSP27.

According to another aspect of the present invention, there is provided a pharmaceutical composition for treating cancer, comprising a nucleic acid coding HSP27.

According to another aspect of the present invention, there is provided a method of inhibiting growth of vascular endothelial cells in vitro using HSP27.

According to another aspect of the present invention, there is provided a method of screening for active substances for inhibiting angiogenesis, the method comprising treating vascular endothelial cell lines with each specimen; measuring the content of HSP27 in the vascular endothelial cell lines; and selecting a specimen in which the HSP27 content in the vascular endothelial cell lines are increased as compared to a control group.

According to another aspect of the present invention, there is provided a method of screening for active substances for treating cancer, the method including treating vascular endothelial cell lines with each specimen; measuring the content of HSP27 in the vascular endothelial cell lines; and selecting a specimen in which HSP27 content in the vascular endothelial cell lines are increased as compared to a control group.

Hereinafter, the present invention is described in greater detail.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein. All publications mentioned herein are incorporated herein in their entirety.

As provided by the present invention, a pharmaceutical composition for inhibiting angiogenesis and a pharmaceutical composition for treating cancer are featured in containing heat shock protein 27 (HSP27). That is based on the present inventors' first discovery that VEGFR2 phosphorylation is reduced by HSP27, VEGFR2 phosphorylation is increased when a function of HSP27 is inhibited, growth of vascular endothelial cells is reduced as a result of actually treating the vascular endothelial cells with HSP27, and HSP27 has an anti-cancer effect when it is administered into an animal having a cancer.

Figure 1:
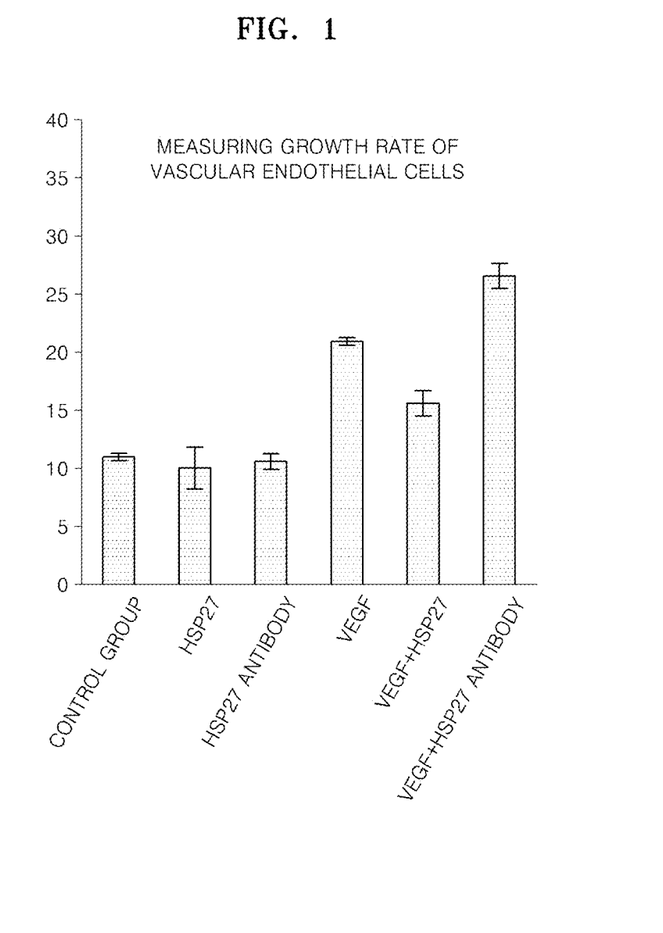
FIG. 1 is a graph showing the results of measuring changes in growth of vascular endothelial cells due to VEGF by using a MTT proliferation assay when HUVEC were treated with HSP27 protein or HSP27 neutralizing antibody.
Figure 2:
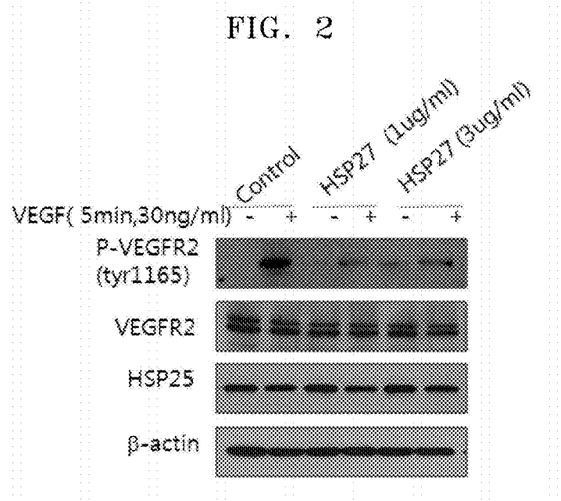
FIG. 2 is an image of the results of measuring degrees of VEGF-induced phosphorylation of VEGFR2 by using a western blotting method when HUVEC was treated with HSP27 proteins.
Figure 3:
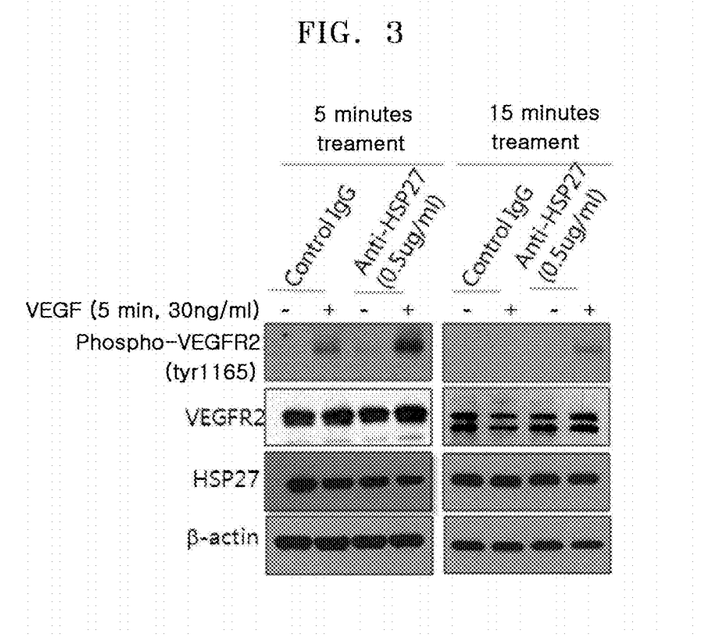
FIG. 3 is an image of the results of measuring degrees of VEGF-induced phosphorylation of VEGFR2 by using the western blotting method when HUVEC was treated with HSP27 neutralizing antibodies.
Figure 4:
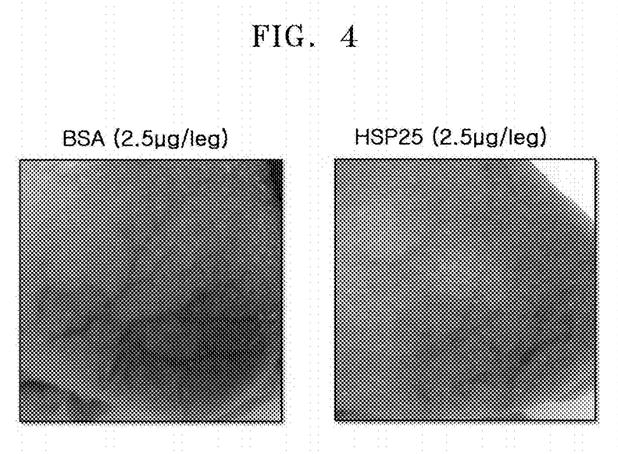
FIG. 4 shows images of thighs of mice of a control group and an HSP25 only-administered group on 10 days after starting HSP25 administration to mice after forming tumor in the mice by injecting colon cancer cell lines to a thigh of each mouse.
Figure 5:
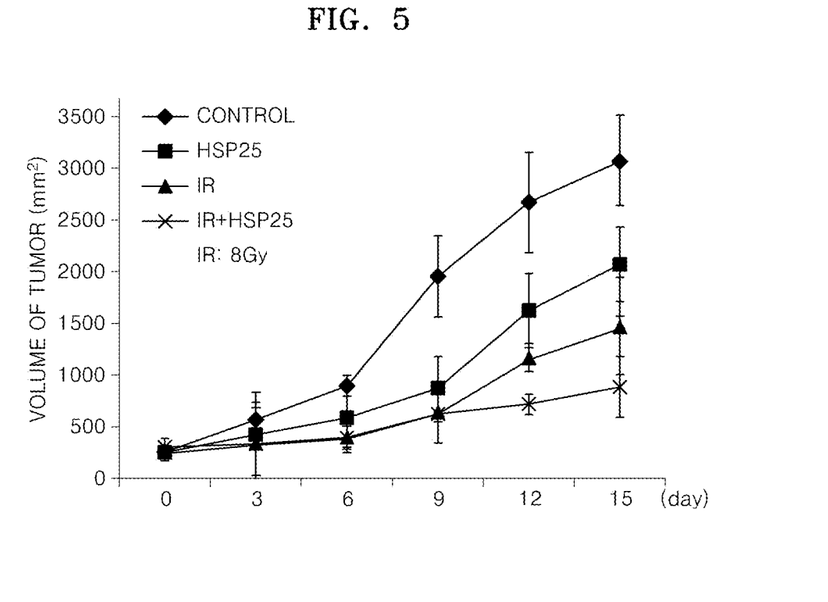
FIG. 5 is a graph showing results of measured volume of tumor in each group of mice of the control group, the HSP25 only-administered group, a radiation only-administered group, and combination of HSP25 and radiation-administered group after forming the tumor in the mice by injecting colon cancer cell lines to a thigh of each mouse.

The present inventors specifically made experiments and found out the following things. Particularly, when a human vascular endothelial cells (HUVEC) culture is treated with vascular endothelial growth factor (VEGF) only, or is treated with VEGF after it is treated with HSP27 protein or HSP27 neutralizing antibody, a growth rate of the vascular endothelial cells is increased in the VEGF only—treated group compared to a control group, a growth rate of vascular endothelial cells is significantly decreased in the combination of HSP27 and VEGF-treated group compared to the VEGF only—treated group, and a growth rate of vascular endothelial cells is significantly increased in the combination of HSP27 neutralizing antibody and VEGF combination—treated group compared to the VEGF only-treated group (FIG. 1). Also, after treating a HUVEC culture with HSP27 protein or HSP27 neutralizing antibody, the HUVEC culture was treated with VEGF, and then the amounts of phsopho-VEGFR2, VEGFR2, and HSP27 were measured. As a result, in the case of the HSP27 protein-treated group, an amount of phospho-VEGFR2 significantly decreased compared to the control group (administered with IgG), and the amounts of VEGFR2 and HSP27 had almost no change (FIG. 2). In the case of the HSP27 neutralizing antibody-treated group, an amount of phosphor-VEGFR2 significantly increased compared to the control group (administered with IgG), and the amounts of VEGFR2 and HSP27 had almost no change (FIG. 3). Also, colon cancer cell lines are injected to a thigh of a mouse to grow a tumor, and then HSP25 protein is administered to the mouse. As a result, it was shown that the HSP25 protein inhibited excessive formation of tumor blood vessels and inhibited growth of the colon cancer cell lines (FIGS. 4 and 5).

Therefore, it is shown that HSP27 inhibits growth of vascular endothelial cells and HSP27 function inhibitor (e.g., HSP27 neutralizing antibody) promotes growth of vascular endothelial cells. It can be inferred that such results are caused by a function of HSP27 which inhibits phosphorylation of VEGFR2. Also, it can be inferred that HSP27 has an anti-cancer effect by inhibiting growth of vascular endothelial cells. Thus, it can be said that HSP27 or a material promoting expression of HSP27 is effective in inhibiting angiogenesis and thus it is effective for treating a malignant tumor.

Therefore, an aspect of the present invention provides a pharmaceutical composition for inhibiting angiogenesis, comprising HSP27.

Said angiogenesis may be accompanied by a disease, such as growth and metastasis of a malignant tumor, age-related macular degeneration, rheumatoid arthritis, diabetic retinopathy, psoriasis, or chronic inflammation, but is not limited thereto. Also, angiogenesis may be accompanied by any ailments which are caused or progressed by angiogenesis.

Also, the present invention provides a pharmaceutical composition for treating cancer, comprising HSP27.

The cancer may be colon cancer, pancreatic cancer, colorectal cancer, prostate cancer, kidney cancer, melanoma, bone-metastatic cancer in prostate cancer, ovarian cancer, or hematologic malignancy, but is not limited thereto, and the cancer includes any cancer in which involve angiogenesis.

The amino acid sequence and nucleic acid sequence of HSP27 contained in the pharmaceutical composition for inhibiting angiogenesis and the pharmaceutical composition for treating cancer are registered in NCBI Gen Bank Accession Number: NP_001531.1 and NM_001540.3. HSP27 contained in the pharmaceutical compositions according to the present invention includes naturally occurring HSP27, HSP originated from recombination, or the variants of the proteins.

Amino acid sequence variants may be a substituted variant which are formed by substituting original one or more amino acids with another amino acid sequence with a similar polarity. An amino acid may be substituted by another amino acid corresponding to the same type to which the original amino acid belongs. The type of amino acid may be for example non-polar (hydrophobic) amino acid (e.g., alanine, leucine, isoleucine, valine, proline, phenylalaline, tryptophan, methionine, etc.), polar neutral amino acid (e.g., glycine, serine, threonine, cysteine, tyrosine, asparagines, glutamine, etc.), positive charge (basic) amino acid (e.g., arginine, lysine, histidine, etc.), or negative charge (acidic) amino acid (e.g., aspartic acid, glutamic acid, etc.).

The other amino acid sequence variant may be a variant by deletion, insertion, or combination thereof.

Site-directed mutagenesis of a nucleotide in DNA that codes HSP27 protein may be produced by the processes that DNA encoding variants are prepared by using common cassette mutagenesis or a well-known technique in the art, and then the DNA is expressed through recombinant cell culture to prepare an amino acid sequence variant. The amino acid sequence variant has the same biological activity as its wild-type. Substitution of amino acid is typically substitution of a single nucleotide, but as long as the amino acid has the same biological activity, substitution of two or more amino acids is possible. Also, the insertion may be normally achieved with a continuous sequence of about 1 to 20 amino acids, but insertion of longer amino acids sequence may also be possible. A range of deletion is normally about 1 to 30 amino acid residues, but in some cases, a deletion of longer amino acids sequence, such as deletion of one of the domains, is possible. A variant is a functional equivalent that has the same biological activities as its wild type, but if necessary, a variant with transformed protein characteristics may be selected.

Also, the HSP27 protein may be modified after translation including myristylation, phosphorylation, glycosylation, or proteolytic cleavage.

The HSP27 protein may be obtained by separating from a natural resource using a well-known method in the art, by using a chemical synthesis method, or by introducing a recombinant expression vector that codes HSP27 protein into an appropriate host, culturing the resulting transfactants, and separating HSP27 from the transfactants.

Separation and purification of HSP27 protein from a culture medium or cell extract may be performed by many known methods. Examples of the separation and purification methods include a method using solubility such as salt precipitation and solvent precipitation, a method using a difference between molecular weights such as dialysis, ultrafiltration, gel filtration, and SDS-polyacrylamide gel electrophoresis, a method using a difference between charges such as ion-exchange column chromatography, a method using a difference between hydrophilicity such as reversed-phase high-performance liquid chromatography, and a method using a difference between isoelectric points such as isoelectric focusing electrophoresis.

Also, according to another aspect of the present invention, a pharmaceutical composition for inhibiting angiogenesis, containing a nucleic acid coding HSP27, is provided.

Angiogenesis may be accompanied by a disease such as growth and metastasis of a tumor, age-related macular degeneration, rheumatoid arthritis, diabetic retinopathy, psoriasis, or chronic inflammation, but is not limited thereto. Also, angiogenesis may be any angiogenesis accompanied by any diseases.

Also, another aspect of the present invention provides a pharmaceutical composition for treating cancer, comprising a nucleic acid coding HSP27.

The cancer may be colon cancer, pancreatic cancer, colorectal cancer, prostate cancer, kidney cancer, melanoma, metastatic prostate cancer, ovarian cancer, or hematologic cancer, but is not limited thereto, and the cancer includes any cancer involving angiogenesis.

The nucleic acid contained in the pharmaceutical composition of the present invention is a sequence coding HSP27 which may be obtained by separating from nature or by artificially synthesizing and transforming.

The nucleic acid sequence may be a single or double stranded chain, and a DNA molecule (genomic, cDNA, or synthesis) or an RNA molecule. The RNA molecule may include a HnRNA molecule corresponding to a DNA molecule including intron and a mRNA molecule that does not include intron. Also, the RNA molecule may include an additional coding sequence or a non-coding sequence.

The nucleic acid coding HSP27 may be transformed by substitution, deletion, or insertion of one or more nucleic acids, and the protein expressed as a result of the transformation should not be changed in the aspects of biological function of the original protein. The transformation includes transformation of heterologous genes to homologous genes.

The nucleic acid coding HSP27 may be provided as a recombinant expression vector in which the sequence is operatively linked to a vector. The vector includes a plasmid, phage, cosmid, or viral vector. The vector may self-replicate or may be integrated to host DNA.

The HSP27 nucleic acid molecule may bind to an expression control sequence, such as a promoter/enhancer sequence, and other sequences necessary for transcription, translation, or processing. The control sequence includes a tissue-specific control and/or inductive sequence in addition to a sequence directing constitutive expression of the nucleotides. Design of the expression vector may be determined by factors such as host cells for the transfection, a desired level of expression, and the like.

The expression vector expressing HSP27 may be preferably a virus vector including, for example, a replication-defective retrovirus, adenovirus, or adenovirus-related virus. The virus vector needs to satisfy the following criteria: (1) the virus vector should be capable of infecting desired cells, and thus a virus vector having an appropriate host range needs to be selected, (2) the delivered genes should be able to be preserved and expressed in the cells for an appropriate period of time, and (3) the virus vector should be safe for the host. Other virus vectors that may be used for delivering the genes into the cells include murine leukemia virus (MLV), JC, SV40, polyoma, Epstein-Barr virus, papilloma virus, vaccinia, polio virus, herpes virus, sindbis virus, lenti virus, and other human or animal virus.

Also, the pharmaceutical compositions comprising HSP27 of the present invention may be administered by being formulated as a formulation for topical administration or an injection according to a common method known in the pharmaceutical field.

The formulation for topical administration or injection may be manufactured according to an injection manufacturing method commonly known in the art.

The formulation for topical administration includes a liquid phase or semi-liquid phase formulation appropriate for penetration to a treatment-needed area through the skin. An example of the liquid phase formulation may be a topical solution, but is not limited thereto. Examples of the semi-liquid phase formulation may be liniment, lotion, cream, ointment, paste, gel, emugel, or the like, but are not limited thereto. The pharmaceutical formulations are commonly used and commonly known to one of ordinary skill in the art of pharmaceutical formulations.

The topical solution of the present invention may be manufactured as a watery or oily solution or a suspension. This formulation may be manufactured by dissolving a pharmaceutical compound in an appropriate watery solution of a bactericidal agent, fungicide, and/or an appropriate preserving agent preferably including a surfactant. A solvent appropriate for manufacturing an oily solution may include glycerol, diluted alcohol, or propylene glycol.

The lotion and liniment according to the present invention include a sterilized watery solution and a solution selectively containing germicide that is appropriate to be applied to skin. Also, the lotion and liniment may include a formulation that promotes drying and cooling the skin, such as alcohol or acetone, and/or a humectant, such as glycerol or oil such as castor oil or peanut oil.

The cream, ointment, or paste is a semi-solid formulation. The semi-solid formulation may be manufactured solely or as a solution or suspension in watery or non-watery fluid with a help of an appropriate machine in addition to an oily or non-oily base by mixing a finely divided salt or a powder-type salt that is pharmaceutically available. The base may include a hydrocarbon. Examples of the hydrocarbon may be a hard, soft, or liquid paraffin, glycerol, wax, metal soap, mucus, a natural oil (e.g., almond oil, corn oil, peanut oil, or olive oil), wool fat, derivatives thereof, and/or fatty acid (e.g., stearic acid or oleic acid), but are not limited thereto. The formulation may contain a surfactant, such as a cationic, anionic, or non-ionic surfactant. Examples of the surfactant may be sorbitan ester or a polyoxyethylene derivative thereof (e.g., polyoxyethylene fatty acid ester), and a carboxymethylene derivative thereof (e.g., carbopol). The formulation may include a suspending agent such as natural gum, a cellulose derivative inorganic material such as silica, and other components such as lanolin. In a case of the ointment, polyethylene glycol 540, polyethylene glycol 3350, and propyl glycol may also be used as mixing with the pharmaceutical compound.

The gel or emugel formulation includes any gel-forming agents that are commonly used in a pharmaceutical formulation. Examples of the random gel-forming agent may be cellulose derivatives such as methyl cellulose, hydroxyethyl cellulose, and carboxymethyl cellulose; vinyl polymers such as polyvinyl alcohol and polyvinylpyrrolidone; and carboxypolymethylene derivatives such as carbopol. Alternatively, another gel-forming agent that may be used in the present invention includes pectin or gum (e.g.: gum Arabic, gum tragacanth, alginate, carrageenate, agar, and gelatin. Also, the gel or emugel formulation may include additives commonly used in a type of formulation, such as preservatives, antioxidants, stabilizing agents, coloring agents, or aromatics.

The excipients and additives used in the formulations as mentioned above and a method of preparing the formulations may be selected and prepared according to a widely-known method in the art (e.g., methods disclosed in the latest version of Remington's Pharmaceutical Science).

A dose and time for administering the pharmaceutical compositions containing HSP27 of the present invention depend on age, gender, physical condition, and weight of a subject to be administered the pharmaceutical compositions, route and number of administrations, and a formulation of drug. An amount of an administration per day may be in a range of about 0.01 ug/kg to about 10 g/kg, and preferably, in a range of about 0.01 mg/kg to about 100 mg/kg.

An effective dose of the pharmaceutical composition comprising a nucleic acid that codes HSP27 of the present invention may be easily determined by considering factors such as size, weight, degree of disease progression, age, physical condition, gender, route of administration, and local or systemic administration. In general, an effective dose of the nucleic acid that codes HSP27 of the present invention includes an intercellular concentration in a range of about 1 nM to about 100 nM at a disease area or an area nearby the disease area. If necessary, the nucleic acid coding HSP27 may be administered in a higher or lower concentration than the range above.

The nucleic acid coding HSP27 protein of the present invention may be administered into a subject by direct injection, as itself combined with a delivery agent, or as a recombinant plasmid or a virus vector expressing the HSP27 protein. In the case of the virus vector, an amount of a recombinant virus including the virus vector may be in a range of about $10^3$ pfu/kg to about $10^{12}$ pfu/kg. The appropriate delivery agent includes lipofectin, lipofectamine, cellfectin, polymer cation (e.g., polylysine), or liposome. The pharmaceutical composition including the nucleic acid coding HSP27 protein of the present invention may be delivered into the cells using a gene gun, ultrasound, or electric shock.

Also, according to the present invention, HSP27 inhibits phosphorylation of VEGFR2, and reduces the growth of vascular endothelial cells, and thus may be used to inhibit growth of vascular endothelial cells.

Thus, according to another aspect of the present invention, a method of inhibiting the in vitro growth of endothelial cells using HSP27 is provided.

HSP27 may be naturally occurring HSP27, HSP27 originated from recombination, or the variants of the proteins as described above, and the inhibition of vascular endothelial cell growth may be enabled by simply adding the naturally-occurring HSP27, HSP27 originated from recombination, or the variants of the proteins to the vascular endothelial cells desired to be inhibited.

Also, according to the present invention, HSP27 protein inhibits phosphorylation of VEGFR2, and reduces angiogenesis, and thus active substances for inhibiting angiogenesis may be selected by selecting a material that increases expression of HSP27 among unknown materials.

Therefore, according to another aspect of the present invention, there is provided a method of screening for active substances for inhibiting angiogenesis based on the discovery that HSP27 protein inhibits angiogenesis by inhibiting phosphorylation of VEGFR2.

The method of screening for active substances for inhibiting angiogenesis comprises treating vascular endothelial cell lines with each specimen; measuring the content of HSP27 in each of the respective vascular endothelial cell lines; and selecting a specimen in which the HSP27 content in the vascular endothelial cell lines are increased as compared to a control group.

Also, according to another aspect of the present invention, there is provided a method of screening for active substances for treating cancer based on discovery that HSP27 protein inhibits angiogenesis by inhibiting phosphorylation of VEGFR2.

The method of screening for active substances for treating cancer comprises treating vascular endothelial cell lines with each specimen; measuring the content of HSP27 in each of the respective vascular endothelial cell lines; and selecting a specimen in which the HSP27 content in the vascular endothelial cell lines are increased as compared to a control group.

The content of HSP27 may be determined by, for example, measuring an amount of mRNA of HSP27 by using a Northern blot method or measuring an amount of expressed HSP27 protein by using an HSP27 protein antibody, and the method may be any known method in the art.

Advantageous Effects

As described above, HSP27 or the nucleic acid coding HSP27 according to the present invention is effective for inhibiting angiogenesis, and due to the angiogenesis inhibiting effect, the HSP27 or the nucleic acid coding HSP27 is effective in treating various diseases that are related to angiogenesis. Also, HSP27 or the nucleic acid coding HSP27 according to the present invention may be effectively used in treating cancer due to the angiogenesis inhibiting effect.

In addition, active substances for inhibiting angiogenesis and active substances for treating cancer may be screened by measuring changes in an amount of HSP27. The technology according to the present invention is an advanced technology that discovers new medical targets by systemic study of signal transfer between proteins in cells and the signal mapping.

BEST MODE

Hereinafter, membranes for alveolar bone regeneration according to exemplary embodiments of the present invention will be described in greater detail with reference to the attached drawings.

Experimental Method

1) Culture of cell lines to be used: Human vascular endothelial cells (HUVEC) bought from Lonza were cultured in a culture chamber at a temperature of 37° C. in a 5 CO2 condition using an endothelial growth medium (EGM) including various growth factors necessary for growth of the vascular endothelial cells.

2) Proliferation assay of vascular endothelial cells: The cells were distributed in a 24-well dish with 7000 cells per well and cultured at 37° C. in $CO_2$ for 24 hours.

Opti-MEM (available from GIBGO) including 1% fetal bovine serum (FBS) (available from GIBGO) was treated with 1 ug/ml of HSP27 (available from Stressgen, Canada) or 0.5 ug/ml HSP27 neutralizing antibody (available from Stressgen, Canada) for an hour, and 30 ng/ml VEGF was added thereto, and then after three days, MTT assay was performed in the following manner: First, the medium was removed, the cells were washed with a PBS buffer solution twice, and then 100 ul of 5 mg/ml MTT (Thiazolyl Blue Tetrazolium Bromide) solution was added to each well and allowed to react at 37° C. for 4 hours. After removing the MTT solution, 200 ul of 4 mM HCl solution was added to the cells, the solution was shaken in Shaker for 15 minutes to allow the reaction to occur, and light absorptivity was measured in a contrast wavelength range of about 620 nm to about 590 nm.

3) Protein analysis using electrophoresis and immune response: To analyze protein in the sample, polyacrylamide gel electrophoresis (PAGE) was first performed, and then a western blot was performed. The sample cells were suspended in a dissolution solution of 120 mM NaCl, 40 mM Tris (pH 8.0), and 0.1% NP40 to burst the cells. Next, a predetermined amount of proteins was segregated according to their molecular weights by 10% SDS-PAGE, and then the proteins were moved to a nitrocellulose membrane and analyzed with immunoblotting analysis.

Example 1

Confirmation of Growth Promotion of Vascular Endothelial Cells of HSP Neutralizing Antibody HUVEC lines were treated with 1 ug/ml HSP27 protein or 0.5 ug/ml HSP27 neutralizing antibody for an hour and then treated with 30 ng/ml of human vascular endothelial growth factor (VEGF). After 3 days, the degrees of cell growth were measured with the MTT analyzing method. The results of the degrees of cell growth of an HSP27 solely-treated group, an HSP27 neutralizing antibody solely-treated group, a VEGF solely-treated group, a VEGF and an HSP27 combined-treated group, and a VEGF and HSP27 neutralizing antibody combined-treated group are shown in FIG. 1.

FIG. 1 is a graph showing the results of measuring changes in growth of vascular endothelial cells due to VEGF by using a MTT proliferation assay when HUVEC were treated with HSP27 protein or HSP27 neutralizing.

Referring to FIG. 1, a growth rate of vascular endothelial cells of the VEGF and HSP27 combined-treated group was lower than that of the VEGF solely-treated group. A growth rate of vascular endothelial cells of the VEGF and HSP27 neutralizing antibody combined-treated group significantly increased compared to that of the VEGF solely-treated group. Each of the HSP27 solely-treated group and HSP27 neutralizing antibody solely-treated group did not show any change in a growth rate of vascular endothelial cells.

Example 2

Confirmation of Promoting Effect of VEGFR2 Phosphorylation of HSP27 Neutralizing Antibody HUVEC lines were treated with 1 ug/ml HSP27 protein or 0.5 ug/ml HSP27 neutralizing antibody for an hour and then treated with 30 ng/ml of human VEGF for 5 minutes. Then, the cells were fractioned, and a western blotting was performed using phospho-VEGFR2, VEGFR2, and HSP27 neutralizing antibody (available from Stressgen, Canada). The western blotting was performed using a β-actin antibody to confirm equal loading. The results of measuring of phospho-VEGFR2, VEGFR2, and HSP27 in a HSP27 protein-treated group are shown in FIG. 2, and the results of measuring phospho-VEGFR2, VEGFR2, and HSP27 of an HSP27 neutralizing antibody treated group are shown in FIG. 3.

FIG. 2 is an image of the results of measuring degrees of VEGF-induced phosphorylation of VEGFR2 by using the western blotting method when HSP27 proteins were treated with HUVEC.

FIG. 3 is an image of the results of measuring degrees of VEGF-induced phosphorylation of phosphorylation of VEGFR2 by using the western blotting method when HUVEC were treated with HSP27 neutralizing antibodies.

Referring to FIG. 2, when the cells were pre-treated with 1 ug/ml and 3 ug/ml HSP27 proteins, it was confirmed that VEGF-induced phosphorylation of VEGFR2 significantly decreased. On the other hand, the amounts of VEGFR2 expression and HSP27 expression were not affected.

Referring to FIG. 3, when the cells were pre-treated with HSP27 neutralizing antibody, it was confirmed that VEGF-induced phosphorylation of VEGFR2 significantly increased. On the other hand, the amounts of VEGFR2 expression and HSP27 expression were not affected.

Example 3

Confirmation of Cancer Formation Inhibition of HSP27 in a Mouse

A total of 28 Balb/C nude mice were divided into 4 groups by 7 mice per group, and each group was named a control group, an HSP25 only-administered group, a radiation only-administered group, or the combination of HSP25 and radiation-administered group.

$1 \times 10^6$ mouse colon cancer cell lines CT26 were injected to a thigh of each of the Balb/C nude mice, and when a size of the tumor became 200 mm$^3$, 2.5 ug of HSP25 protein was injected to the tumor area, and 8 Gy radiation was partially irradiated 1 day after the administration of HSP25 protein. HSP25 protein was injected twice with an interval of three days, and then a size of the tumor of each mouse was observed. The control group was not treated with HSP25 protein and radiation, but instead, bovine serum albumin (BSA) at the same amount as HSP25 was injected. The HSP25 only-administered group was not irradiated but injected with HSP25 only, and the radiation only-administered group was only irradiated without the administration of HSP25.

Next, images of thighs of the mice of the control group and the HSP25 only-administered group on 10 days after starting HSP25 administration are shown in FIG. 4.

Also, the results of measuring a volume of the tumor of each administration group according to date passed after starting HSP25 administration are shown in FIG. 5.

Referring to FIG. 4, it is shown that HSP25 protein inhibits excessive formation of tumor blood vessels and inhibits growth of colon cancer cell lines. Also, referring to FIG. 5, when HSP25 was administered together with radiation, it is shown that a cancer cell growth inhibiting effect significantly increased. Thus, when HSP25 is solely administered, cancer growth may be inhibited, and in addition, when HSP25 is administered as combined with radiation, an anti-cancer effect may be significantly further increased.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A method for inhibiting angiogenesis, the method comprising selecting a subject in need of inhibiting angiogenesis; and administering to the subject in need of inhibiting angiogenesis an effective amount of a pharmaceutical composition comprising a heat shock protein 27 (HSP27), thereby inhibiting angiogenesis.

2. The method of claim 1, wherein HSP27 is a recombinant protein.

3. The method of claim 1, wherein the angiogenesis is accompanied by growth and metastasis of a malignant tumor, age-related macular degeneration, rheumatoid arthritis, diabetic retinopathy, psoriasis, chronic inflammation, or a combination thereof.

4. A method for treating cancer, the method comprising selecting a subject with cancer; and administering to the subject with cancer an effective amount of a pharmaceutical composition comprising a heat shock protein 27 (HSP27).

5. The method of claim 4, wherein the cancer is colon cancer, pancreatic cancer, colorectal cancer, prostate cancer, kidney cancer, melanoma, bone-metastatic cancer in prostate cancer, ovarian cancer, or hematologic cancer.

* * * * *